(12) United States Patent
Matsumoto (10) Patent No.: US 6,832,835 B2
(45) Date of Patent: Dec. 21, 2004

(54) FUNDUS IMAGE-TAKING APPARATUS AND METHOD

(75) Inventor: Kazuhiro Matsumoto, Tochigi (JP)

(73) Assignee: Canon Kabushiki Kaisha, Tokyo (JP)

(*) Notice: Subject to any disclaimer, the term of this patent is extended or adjusted under 35 U.S.C. 154(b) by 137 days.

(21) Appl. No.: 10/263,956

(22) Filed: Oct. 4, 2002

(65) Prior Publication Data

US 2003/0071966 A1 Apr. 17, 2003

(30) Foreign Application Priority Data

Oct. 15, 2001 (JP) ......................................... 2001-317079

(51) Int. Cl.⁷ .......................... A61B 3/14; G03B 29/00; G03B 15/03
(52) U.S. Cl. ......................... 351/206; 396/18; 396/164; 351/221; 351/246
(58) Field of Search .............................. 351/200, 205, 351/206, 221, 246; 396/18, 48, 213, 155, 164

(56) References Cited

U.S. PATENT DOCUMENTS

| | | | |
|---|---|---|---|
| 4,429,969 A | * | 2/1984 | Saegusa ...................... 396/161 |
| 4,773,749 A | * | 9/1988 | Ohtomo et al. .............. 351/206 |
| 4,952,049 A | | 8/1990 | Matsumoto .................. 351/211 |
| 5,455,644 A | | 10/1995 | Yazawa et al. .............. 351/206 |
| 5,530,493 A | * | 6/1996 | Suzuki ........................ 351/206 |
| 6,158,864 A | | 12/2000 | Masuda et al. .............. 351/206 |
| 6,273,565 B1 | | 8/2001 | Matsumoto .................. 351/210 |
| 6,278,490 B1 | * | 8/2001 | Fukuda et al. .............. 348/362 |
| 6,327,375 B1 | | 12/2001 | Matsumoto et al. ......... 382/117 |
| 6,456,787 B1 | | 9/2002 | Matsumoto et al. ......... 396/106 |
| 6,575,571 B2 | * | 6/2003 | Shibata ........................ 351/206 |

FOREIGN PATENT DOCUMENTS

JP 2801318 7/1998

* cited by examiner

Primary Examiner—Brian L. Casler
Assistant Examiner—John R Sanders
(74) Attorney, Agent, or Firm—Fitzpatrick, Cella, Harper & Scinto (57) ABSTRACT

A fundus image-taking and recording apparatus emits an appropriate amount of light at the time of taking an image by determining an appropriate light exposure from the amount of observation light during observation. In particular, even when the brightness varies during fluorescence image-taking, the fundus image-taking apparatus can provide an image having adequate brightness by measuring the sensitivity of a television camera for observation to thereby determine an appropriate amount of image-taking light.

12 Claims, 3 Drawing Sheets

FUNDUS IMAGE-TAKING APPARATUS AND METHOD

BACKGROUND OF THE INVENTION

1. Field of the Invention

The present invention relates to an ophthalmological image-taking apparatus for use in an ophthalmic clinic or the like and to a method for changing a gain in the ophthalmological image-taking apparatus.

2. Description of the Related Art

For example, an ophthalmological image-taking apparatus disclosed in Japanese Patent No. 2,801,318 performs automatic exposure compensation. To provide an image with an automatically-adjusted light exposure, the image-taking apparatus determines a fundus refractive index from the amount of light illuminating an eye fundus and the amount of light reflected from the eye fundus, and controls the amount of light to be emitted from a fundus image-taking light source on the basis of the refractive index thereof.

In the example of the related art, however, optical members for extracting light flux need to be provided in the optical paths of an illumination optical system and an image-taking optical system.

As a result, a loss in the amount of image-taking light occurs, or mechanisms for inserting and retracting the optical members are required, thus resulting in a complicated structure.

In addition, the image-taking apparatus has problems in that a considerable amount of time is required from when the switch is pressed until an image is actually recorded and the accuracy of the image taking is reduced.

SUMMARY OF THE INVENTION

Accordingly, to overcome the foregoing problems, an object of the present invention is to provide an ophthalmological image-taking apparatus that controls the amount of emission light and that performs high-accuracy image-taking and recording with a simple structure.

Another object of the present invention is to provide a method for changing a gain in the ophthalmological image-taking and recording apparatus.

In order to achieve the foregoing objects, according to the present invention, the amount of light emitted from an image-taking light source for taking and recording an image is controlled in accordance with the amount of light emitted from an observation light source used for observing an eye fundus and with the intensity of a video signal.

In addition, in order to achieve the foregoing objects, according to the present invention, the amount of light emitted from the image-taking light source for taking and recording an image is controlled in accordance with the amount of light emitted from the observation light source for observing the eye fundus and with a gain for amplifying the video signal to a signal having a predetermined intensity.

Additionally, in order to achieve the foregoing objects according to the present invention, a gain for taking and recording an image of an eye to be examined is stored in storing means and the gain stored in the storing means is controlled in accordance with a video signal output, at the time of image-taking, from an image-capturing means.

Further objects, features and advantages of the present invention will become apparent from the following description of the preferred embodiments with reference to the attached drawings.

DESCRIPTION OF THE PREFERRED EMBODIMENT

Figure 1:
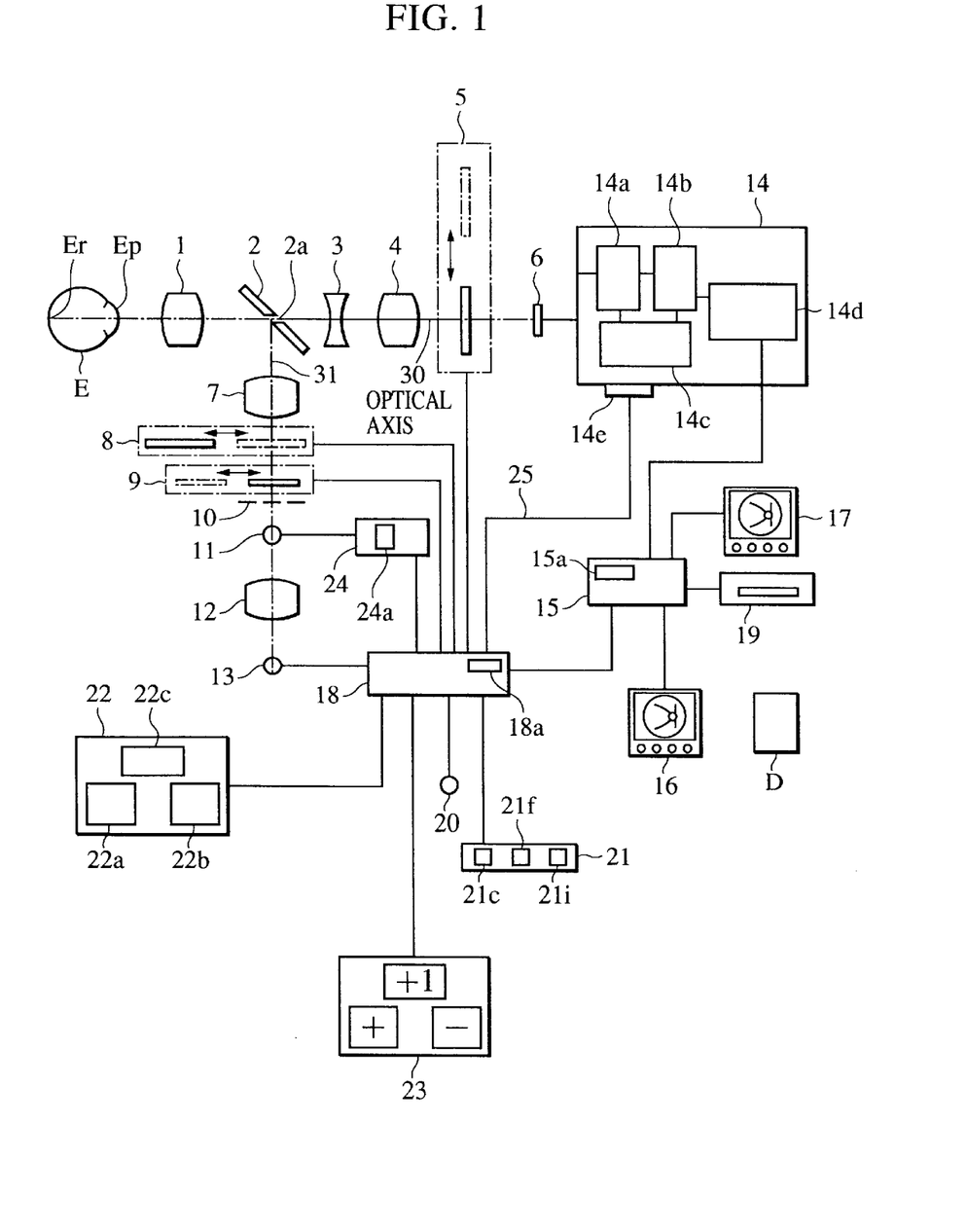
FIG. 1 is a block diagram of a fundus camera.

The present invention will now be described in conjunction with the embodiment thereof with reference to the attached drawings. FIG. 1 is a block diagram of a fundus camera according to the embodiment of the present invention. An objective lens 1 is arranged in front of an eye E to be examined, and a fundus image-taking and recording system is arranged behind the objective lens 1. The fundus image-taking system includes an aperture mirror 2, an image-taking diaphragm 2a provided in the aperture of the aperture mirror 2, a focus lens 3 capable of moving along an optical path 30, an image-taking lens 4, an infrared-fluorescence barrier filter 5 that can be inserted into and retracted from the optical path 30 to block excitation light and to transmit only fluorescence, and an image-capturing element 6.

A fundus illumination system is provided in the incident direction of the aperture mirror 2. The fundus illumination system includes a relay lens 7, an infrared cut filter 8 that can be inserted into and retracted from an optical path 31, an infrared-fluorescence excitation filter 9 that can be inserted into and retracted from the optical path 31, a diaphragm 10 having a ring aperture, a strobe light source 11 for flashing light, a condenser lens 12, an observation light source 13, such as a halogen lamp, for emitting continuous light are arranged in sequence from the aperture mirror 2 side.

A signal output from the image-capturing element 6 is input to an image control circuit 15 via a television circuit 14. The television circuit 14 includes an amplifying circuit 14a, a signal determination circuit 14b, a gain setting circuit 14c constituted by an AGC (auto gain control) circuit, and a video-signal generation/control circuit 14d for generating a video signal and controlling the color temperature. The amplifying circuit 14a further includes a communication port 14e for externally setting conditions, such as the gain, for the camera and for obtaining information from the camera.

The image control circuit 15 is connected to, for example, a monochrome monitor 16, a color monitor 17, a control circuit 18, and an image recorder 19. The image recorder 19 is a device that is capable of performing writing onto or reading from a recording medium D, such as an MO, MD, DVD-RAM, VTR tape, hard disk, or the like, which is capable of maintaining recorded data without an external power supply.

The control circuit 18 is connected to an image-taking switch 20, an image-taking mode selection switch 21, a light control switch 22 for adjusting the amount of observation light, an exposure compensation switch 23 for compensating for the exposure of a still image, and a strobe-light emission control circuit 24. The image-taking mode selection switch 21 is used for selecting a color image-taking mode, a visible-fluorescence image-taking mode, or an infrared-fluorescence image-taking mode. The control circuit 18 is connected to the communication port 14e, provided at the television circuit 14, via a control line 25.

In addition, the strobe light source 11 is connected to the strobe-light emission control circuit 24 for controlling the amount of flash light. The strobe-light emission control circuit 24 includes a capacitor 24*a* for controlling the amount of flash light.

For color image-taking, an operator asks a subject to be seated in front of the fundus camera, and performs alignment of the fundus camera with the eye E while observing a moving image of a fundus Er. Thereafter, the operator operates a switch 21*c* of the image-taking mode selection switch 21 to set the camera into a color image-taking mode. Upon detecting an input indicating the operation of the switch 21*c*, the control circuit 18 retracts the infrared-fluorescence barrier filter 5 from the optical path 30 and retracts the infrared-fluorescence excitation filter 9 from the optical path 31, inserts the infrared cut filter 8 into the corresponding optical path, and sends a control command to the communication port 14*e* via the control line 25. In accordance with a determination by the signal determination circuit 14*b*, the gain setting circuit 14*c* sets the camera into an AGC mode for automatically setting the gain of the amplifying circuit 14*a*.

In addition, light is emitted from the observation light source 13, is focused by the condenser lens 12, and passes through the strobe light source 11 and the ring aperture of the diaphragm 10. Infrared components of the light are removed by the infrared cut filter 8, and the resulting light is transmitted through the relay lens 7 and is reflected to the left, in FIG. 1, by a mirror portion provided around the aperture of the aperture mirror 2. The reflected light passes through the objective lens 1 and the pupil Ep of the eye E and illuminates the fundus Er. An image of the fundus Er thus illuminated is again transmitted through the objective lens 1, the image-taking diaphragm 2*a*, the focus lens 3, and the image-taking lens 4, is captured by the image-capturing element 6, and is converted into an electrical signal.

The electrical signal is input to the amplifying circuit 14*a* and is initially amplified by a minimum gain. The amplifying circuit 14*a* is a known amplifying circuit and is designed so that it can amplify a signal in a range of 0 to 20 dB. The electrical signal amplified by the amplifying circuit 14*a* is input to the signal determination circuit 14*b*, in which the average level of the input electrical signal is compared with a predetermined reference level of, for example, 0.4 V. If the level of the electrical signal from the amplifying circuit 14*a* is lower than the reference level, the gain setting circuit 14*c* increases the gain of the amplifying circuit 14*a* by 1 dB. This operation of increasing the gain of the amplifying circuit 14*a* by the gain setting circuit 14*c* is repeated until the average value of the signal amplified by the amplifying circuit 14*a* exceeds the reference level of 0.4 V. Conversely, if the average level of the electrical signal exceeds 0.7 V, the gain setting circuit 14*c* reduces the gain.

The electrical signal amplified to the predetermined level in the above manner is input to the video-signal generation/control circuit 14*d*, which converts this amplified electrical signal to a video signal and attaches a synchronization signal thereto and inputs the video signal and the attached synchronization signal into the image control circuit 15, and the circuit 15 then transmits this video signal to the monochrome monitor 16, which converts the video signal into a fundus image and displays the fundus image.

When the fundus image displayed on the monochrome monitor 16 is dark or has a high level of noise due to a high gain, the operator operates the light control switch 22 to control the amount of observation light. Operating a switch 22*a* causes the amount of light emitted from the observation light source 13 to increase, and operating a switch 22*b* causes the amount of emission light to decrease, such that a number from 1 to 20 corresponding to the set light intensity is displayed on a display portion 22*c*.

The observer observes the fundus image displayed on the monochrome monitor 16, and after confirming that image-taking preparations are finished, operates the image-taking switch 20 for taking and recording a color still image. In turn, the control circuit 18 detects an input indicating the operation of the image-taking switch 20 and then calculates the amount of image-taking light for taking and recording the still image.

The control circuit 18 obtains, via the communication port 14*e*, information X (dB) concerning a gain that is pre-set in the amplifying circuit 14*a*. Next, the control circuit 18 uses a table stored in the memory 18*a* to convert the amount of light emitted from the observation light source, set by the control circuit 18 and optionally reset by the operator using the light control switch 22, which has a value in the range of 0 to 20, into the amount of image-taking light for taking and recording a still image in accordance with the converted value. This converted value is used by the control circuit 18 to determine the amount of image-taking light P emitted by the strobe light source 11.

Since the strobe light source 11 used for taking and recording a still image emits high-intensity light compared to the observation light source 13, a small gain is sufficient for the amplifying circuit 14*a*. Setting the gain low causes the noise to be reduced, and thus is advantageous in taking and recording a still image in which noise tends to be more frequent. The gain for taking and recording the still image is stored in a memory 18*a* of the control circuit 18.

The amount (lux-sec) of image-taking light P received from the objective lens 1 is determined from the following expression:

$$P = kc \times Q \times 2^{((R-S)/6)}$$

where Q is the amount (lux-sec) of observation light, R is the gain (dB) during observation, S (dB) is the gain for image-taking, and kc is a color coefficient.

The control circuit 18 fixes, via the control line 25, the gain of the amplifying circuit 14*a* to the gain S (dB) for taking and recording a still image, and further controls the video-signal generation/control circuit 14*d* to adjust the color balance and to change the color temperature to 5,600 K. The strobe-light emission control circuit 24 adjusts the amount of electrical charge of the capacitor 24*a* such that the strobe light source 11 flashes the amount of image-taking light P determined as described above.

Subsequently, the observation light source 13 is turned off, and in response to a signal for providing flash light, the strobe light source 11 flashes light to produce the amount P of light due to the electrical charge stored in the capacitor 24*a*. In the same manner as the observation light, the light flux emitted from the strobe light source 11 passes through the ring aperture of the diaphragm 10 and the relay lens 7, and is reflected to the left by the mirror portion provided around the aperture of the aperture mirror 2. The reflected light passes through the objective lens 1 and the pupil Ep and illuminates the fundus Er.

An image of the fundus Er thus illuminated is again transmitted through the objective lens 1, the image-taking diaphragm 2*a*, the focus lens 3, and the image-taking lens 4, is captured by the image-capturing element 6, and is converted into an electrical signal. The amplifying circuit 14*a* amplifies the signal by the gain S, and the signal determination circuit 14*b* determines whether the signal level of the amplified electrical signal is adequate and transmits the electrical signal to the image control circuit 15 via the video-signal generation/control circuit 14d. The image control circuit 15 converts the electrical signal into digital image data, temporarily stores the data in a memory 15a, and then records the data on the recording medium D via the image recorder 19. At the same time, the image control circuit 15 causes the fundus image and the determination result to be displayed on the color monitor 17.

The control circuit 18 issues an instruction, via the communication port 14e, for starting automatic gain control (AGC) using the amplifying circuit 14a, the signal determination circuit 14b, and the gain setting circuit 14c. The control circuit 18 turns off the observation light source 13 and sets the color temperature for the video-signal generation/control circuit 14d to 3,200 K to complete color image-taking and recording operation.

For color image-taking and recording, since the image-taking conditions vary depending on the individual case, the result of the determination described above is not reflected in the gain, stored in the memory 18a, for taking and recording a still image and a compensated value for the amount of image-taking light. Instead, when the observer observes the generated fundus image and determines that the exposure is not adequate, the observer can change the compensated value by operating the light control switch 22. Thus, after detecting an input indicating the operation of the light control switch 22, the control circuit 18 stores the values so that, in the case of increasing the light exposure brightness, a higher priority is given to compensating for the amount of light, and so that, in the case of reducing the light exposure brightness, a higher priority is given to compensating for the gain. This value is then reflected in the next image-taking and recording operation.

For infrared-fluorescence image-taking, when a switch 21i of the image-taking mode selection switch 21 is operated, the control circuit 18 detects an input indicating the operation, inserts the infrared-fluorescence excitation filter 9 into the corresponding optical path 31, and retracts the infrared cut filter 8 from the optical path 31. In the same manner as the color image-taking, light emitted from the observation light source 13 is focused by the condenser lens 12, passes through the strobe light source 11 and the ring aperture of the diaphragm 10, and only light having an infrared-fluorescence excitation wavelength is transmitted by the infrared-fluorescence excitation filter 9. The resulting light passes through the relay lens 7, is reflected to the left by the mirror portion provided around the aperture of the aperture mirror 2, passes through the objective lens 1 and the pupil Ep, and illuminates the fundus Er.

An image of the fundus Er thus illuminated is again transmitted through the objective lens 1, the image-taking diaphragm 2a, the focus lens 3, and the image-taking lens 4, is captured by the image-capturing element 6, and is converted into an electrical signal. The electrical signal is input to the amplifying circuit 14a and is displayed on the monochrome monitor 16 with brightness being adjusted adequately. The operator observes the reflected fundus image, which is caused by fluorescence excitation light, displayed on the monochrome monitor 16 to confirm the position of a region whose image is to be taken and recorded and to confirm whether the focal point is appropriate. After preparations for taking the infrared-fluorescence image are finished, a fluorescent material, such as indocyanine green, for taking an infrared-fluorescence image is injected into a vein of the subject and infrared-fluorescence barrier filter 5 is inserted into the corresponding optical path 30.

The fluorescent material soon reaches the fundus Er, and is excited by excitation light to emit fluorescence. The excitation-light reflected image of the fundus and the fluorescence are again transmitted through the objective lens 1, the image-taking diaphragm 2a, the focus lens 3, and the image-taking lens 4, and the reflected image is screened by the infrared-fluorescence barrier filter 5. A fluorescent image transmitted through the infrared-fluorescence barrier filter 5 is captured by the image-capturing element 6 and is converted into an electrical signal.

In the same manner as for the color image-taking, the electrical signal is input to the gain setting circuit 14c of the television circuit 14, is subjected to AGC, and is converted into a video signal by the video-signal generation/control circuit 14d. The video signal is input into the circuit 15, which in turn, inputs the video signal into the monochrome monitor 16, which converts the video signal into a fundus image and displays the fundus image. The intensity of the fluorescent image varies by a large extent depending on the elapsed time after the injection of the fluorescent material. Immediately after the injection of the fluorescent material, no fluorescent image appears, resulting in a black image on the monochrome monitor 16. In this case, since the signal level from the image-capturing element 6 is low, the gain of the amplifying circuit 14a is set to a maximum value. The intensity of the fluorescent image sharply increases after about 15 seconds has elapsed from the injection of the fluorescent material, and correspondingly, the gain of the amplifying circuit 14a is set to a small value. The intensity of the fluorescence image gradually decreases after about one minute has elapsed from the injection of the fluorescent material. At the same time, the gain of the amplifying circuit 14a is gradually set to a large value.

The operator observes the fluorescence image displayed on the monochrome monitor 16, and after confirming that image-taking preparations are finished, operates the image-taking switch 20 for taking and recording a still image of the fluorescence image. Upon detecting an input indicating the operation of the image-taking switch 20, the control circuit 18 calculates the amount of light to be emitted from the strobe light source 11 for taking and recording the still image, in the same manner as for the color image-taking.

The amount of image-taking light P received from the objective lens 1 is determined from the following expression:

$$P = ki \times Q \times 2^{((R-S)/6)}$$

where Q is the amount of observation light, R is the observation gain (dB), S is the image-taking gain (dB), and ki is an infrared-fluorescence coefficient.

The control circuit 18 fixes the gain of the amplifying circuit 14a to the gain S (dB) via the control line 25, and the strobe-light emission control circuit 24 adjusts the amount of electrical charge of the capacitor 24a so that the amount of light the strobe light source 11 flashes is the amount of the image-taking light P. The observation light source 13 is then turned off, and upon receiving a signal for flashing light, the strobe light source 11 flashes light in the amount of the image-taking light P due to the electrical charge stored in the capacitor 24a. In the same manner as the observation light, the light flux emitted from the strobe light source 11 passes through the ring aperture of the diaphragm 10 and the relay lens 7, is reflected to the left by the mirror portion provided around the aperture of the aperture mirror 2, and only infrared-fluorescence excitation light of the resulting light is transmitted by the infrared-fluorescence excitation filter 9. The excitation light then passes through the objective lens 1 and the pupil Ep and illuminates the fundus Er.

An infrared-fluorescence image and a reflected image thus illuminated are again transmitted through the objective lens 1, the image-taking diaphragm 2a, the focus lens 3, and the image-taking lens 4. Light other than the fluorescence image is blocked by the infrared-fluorescence barrier filter 5, and the resulting image is captured by the image-capturing element 6 and is then converted into an electrical signal. The amplifying circuit 14a amplifies the electrical signal by the gain S, and the signal determination circuit 14b determines the intensity of the signal and sends the signal to the image control circuit 15 via the video-signal generation/control circuit 14d. The image control circuit 15 converts the electrical signal into digital image data, temporarily stores the data in the memory 15a, and records the data onto the recording medium D via the image recorder 19. At the same time, the image control circuit 15 displays the fundus image on the color monitor 17.

The control circuit 18 issues an instruction, via the image control circuit 25, for starting AGC using the amplifying circuit 14a, the signal determination circuit 14b, and the gain setting circuit 14c, and turns off the observation light source 13. The operator repeats the above-described operations to complete the desired fluorescence image-taking.

FIG. 2 is a time chart for fluorescence image-taking. A description will now be given with reference to the time chart shown in FIG. 2 and the flow chart shown in FIG. 3.

Figure 2A:
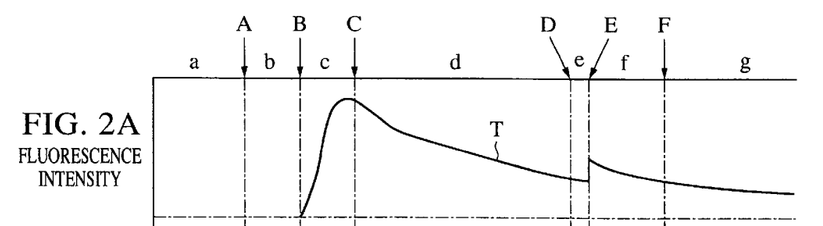
FIG. 2 is a time chart for fluorescence image-taking.
Figure 2B:
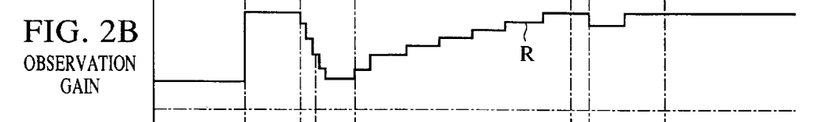
Figure 2C:
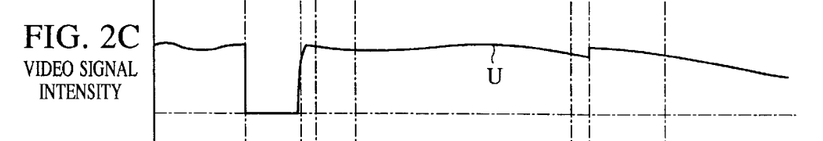
Figures 2D, 2E:
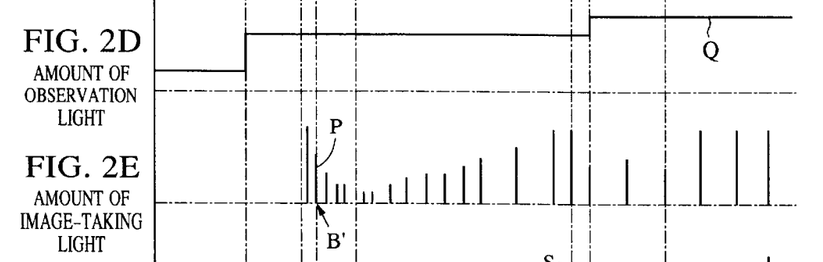
Figure 2F:
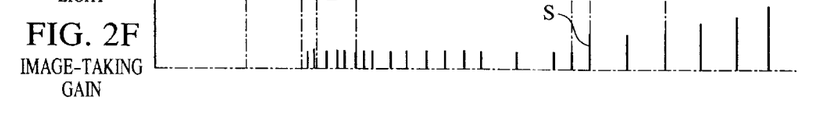

In FIGS. 2A to 2F, the horizontal axis indicates time, and the vertical axis in FIG. 2A indicates the fluorescence intensity T of fluorescence emitted from the fundus Er of the eye E to be examined, the vertical axis in FIG. 2B is the observation gain R of the amplifying circuit 14a, the vertical axis in FIG. 2c is the video signal intensity U of a video signal output from the gain setting circuit 14c, the vertical axis in FIG. 2D is the amount of observation light Q emitted from the observation light source 13, the vertical axis in FIG. 2E is the amount of image-taking light P emitted from the strobe light source 11 for taking and recording a still image, and the vertical axis in FIG. 2F is the image-taking gain S, for taking and recording a still image, of the amplifying circuit 14a. Period a indicates a stage in which only the infrared-fluorescence excitation filter 9 is inserted into the corresponding optical path 31 to perform alignment, as described above, and thus, in period a, fluorescence does not appear.

Since the amount of light reflected from the fundus Er is large, regardless of a small amount of observation light Q, a video signal having an appropriate intensity is provided at a small observation gain R. Time A indicates the time at which a fluorescent material is injected and the infrared-fluorescence barrier filter 5 is inserted into the corresponding optical path 30, and time B indicates the time at which fluorescence begins to appear. Thus, since no fluorescence appears in period b, a video signal is not provided even though the observation gain R is set high. Also, in preparation for the appearance of a fluorescence image, the amount of observation light Q is increased in association with the insertion of the infrared-fluorescence barrier filter 5.

The fluorescence intensity T sharply increases from time B to time C. The observation gain R is thus reduced step-by-step. In accordance with the above-noted expression, the amount of image-taking light P, for example, at time B' is determined from the amount of observation light Q, the observation gain R, and the image-taking gain S which are obtained immediately before the image-taking switch 20 is operated. The fluorescence intensity T after time C decreases gradually. At time D, even though the image-taking and recording is performed with the maximum amount of image-taking light P, the signal determination circuit 14b determines that the video signal intensity U is low. Since the gain S, stored in the memory 18a of the control circuit 18, for taking a still image is changed, after time E, the gain S for taking a still image is set high.

At time E, since the video signal intensity U of the image being observed has begun to decrease, the operator increases the amount of observation light Q by operating the light control switch 22. As a result, both the fluorescence intensity T and the video signal intensity U increase.

After time F, since the fluorescence intensity T has been decreasing, the video signal intensity U continues to decrease even though the observation gain R during observation is at a maximum. At this point, when the gain setting circuit 14c determines that the video signal intensity U is not sufficient even though the amount of image-taking light P is at a maximum, the gain setting circuit 14c sends to the control circuit 18 via the communication port 14e an instruction for increasing the gain S for taking a still image by one level. The control circuit 18 stores the gain S for taking the next still image in the memory 18a. When the image-taking switch 20 is operated subsequently, the stored image-taking gain S is used. Thus, the image-taking gain S is gradually set to a larger value.

Meanwhile, when determining that exposure is inadequate, the operator operates the exposure compensation switch 23 in the same manner as described above, so that an image with compensated exposure can be provided at the next image-taking and recording operation.

Figure 3:
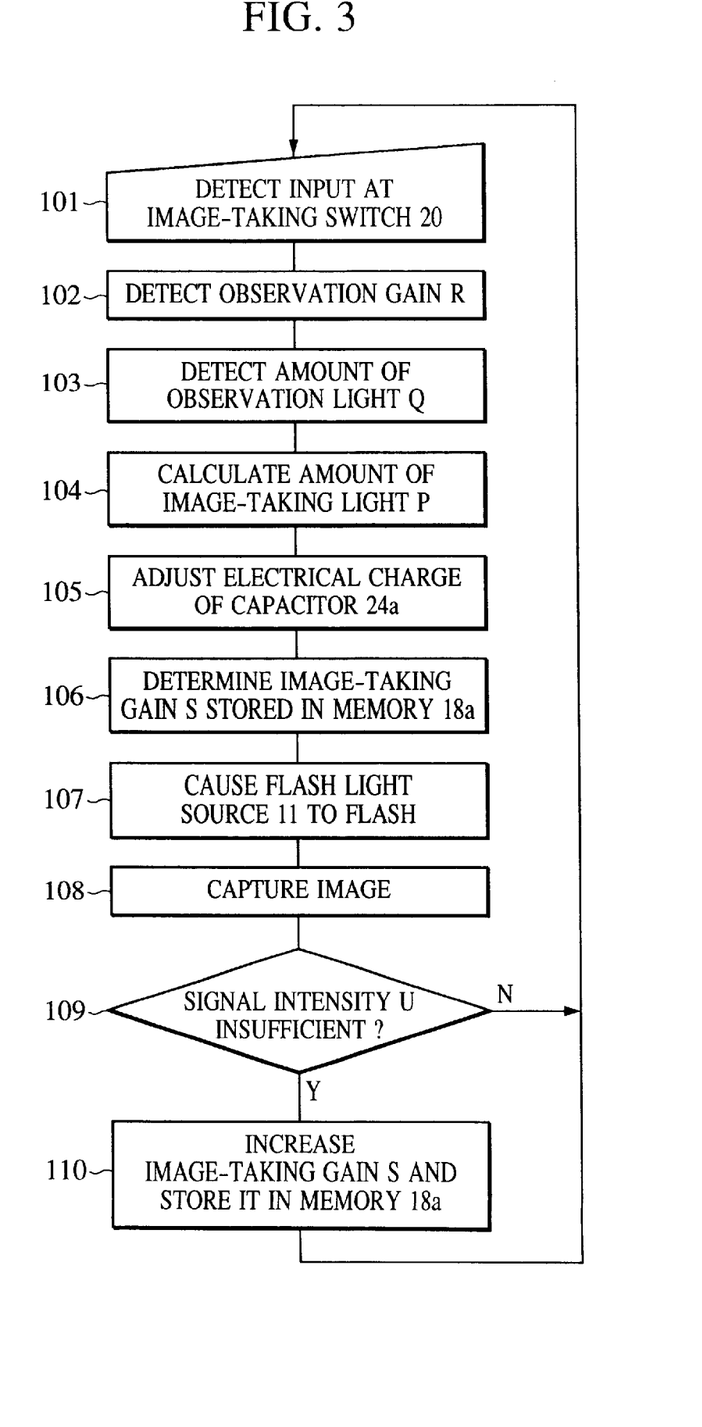
FIG. 3 is a flow chart illustrating the operation of a control circuit.

The operation of the control circuit 18 will now be described with reference to the flow chart of FIG. 3.

In step 101, upon detecting that the image-taking switch 20 is turned on, the control circuit 18 detects the observation gain R in step 102 and detects the amount of observation light Q in step 103 to calculate the amount of image-taking light P in step 104. In accordance with the calculated result, in step 105, the control circuit 18 adjusts the amount of electrical charge of the capacitor 24a to determine the amount of emission light.

Next, in step 106, the control circuit 18 determines the image-taking gain S that is stored in the memory 18a.

In step 107, the control circuit 18 causes the strobe light source 11 to emit light with the amount of light set in step 105 and causes an image to be captured in step 108. In step 109, the control circuit 18 determines whether or not the video signal intensity U is sufficient. If it is insufficient, the control circuit 18 increases the image-taking gain S in step 110 and stores the resultant gain S in the memory 18a. If it is sufficient, no change is made to the image-taking gain S in the memory 18a. In either case, when the image-taking switch 20 is turned on next time, the control circuit 18 uses the value stored in the memory 18a and performs the same operation as the previous one.

The wavelength band of light used for the fluorescence image-taking is narrow compared to color image taking, and thus is less susceptible to the difference between the color temperatures of the observation light source 13 and the strobe light source 11, thereby allowing more accurate adjustment of light exposure.

While the description in the above embodiment has been made for infrared-fluorescence image-taking, the same advantage can be provided for visible-fluorescence image taking by operating a switch 21f of the image-taking mode selection switch 21 and replacing the infrared-fluorescence barrier filter 5 and the infrared-fluorescence excitation filter 9 with a filter for visible-fluorescence image-taking.

While the amount of electric charge stored in the capacitor 24a has been adjusted in order to adjust the amount of image-taking light in the above embodiment, a known circuit that can control the period of light emitted from the strobe light may be used, so that the period of emission light is calculated from the amount of emission light and the period of the emission light is controlled to adjust the amount of emission light. With this arrangement, since no time is required for charging or discharging the capacitor 24a, it is possible to achieve light-exposure control with higher accuracy.

For fluorescence image-taking, after a certain amount of time has elapsed from the injection of a fluorescent material, the intensity of a fluorescence image becomes considerably low. Thus, even maximizing the intensity of emission light of the observation light source 13 and maximizing the gain of the amplifying circuit 14a may not provide a video signal having adequate brightness. In such a case, even if the amount of light emitted from the strobe light source 11, which provides high-intensity light, used for taking a still image is still within the capacity of the strobe light source 11, the amount of emission light for taking the still image cannot be properly calculated. As a result, a still image with adequate brightness cannot be provided.

Accordingly, signals for taking a still image may also be determined, as described above, by the signal determination circuit 14b, and the result of the determination may be stored in the memory 18a so that the result is used for taking the next image. With this arrangement, even when fluorescence is at such a weak level that adequate brightness cannot be provided even with a maximum amount of observation light and with a maximum gain of the camera, an image with adequate brightness can be provided by effectively using the amount of light emitted from the strobe light source 11, which provides high-intensity light, for taking a still image.

In addition, the quality of images are different between an image taken in color and an image taken using fluorescence. That is, in an image taken in color, signals exist for the entire image, which is a typical image, whereas for an image taken in fluorescence, bright portions appear on a black background. Thus, average signal intensities for images that are easy to view vary for each case. Thus, providing the exposure compensation switch 23 and compensating for a light exposure can provide an image having an adequate exposure for both color image-taking and fluorescence image taking.

As described above, the ophthalmological image-taking apparatus of the present invention calculates, using a gain during observation, the amount of emission light for taking a still image. As a result, without providing special detecting means leading to a complicated structure, the ophthalmological image-taking apparatus does not require extra time from when the image-taking switch is operated until an image is actually taken since no moving portion is included, so that an image can be taken at the right moment. In addition, the ophthalmological image-taking apparatus can provide an image having an adequate light exposure and thus can improve image-taking efficiency.

In particular, for fluorescence image-taking, when the intensity of fluorescence images varies dramatically, measuring the sensitivity of a television camera and determining the amount of image-taking light can constantly provide images having adequate light exposures, even when images of an object whose brightness dramatically varies are continuously taken.

While the present invention has been described with reference to what is presently considered to be the preferred embodiment, it is to be understood that the invention is not limited to the disclosed embodiment. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An ophthalmological image-taking apparatus comprising:
    an observation light source configured and positioned to illuminate an eye fundus during observation;
    image-capturing means for capturing an image of the eye fundus;
    first adjusting means for adjusting the amount of light emitted from said observation light source;
    a flash source configured and positioned to illuminate the eye fundus when taking a still image;
    second adjusting means for adjusting the amount of light emitted from said flash source; and
    emission control means for controlling said second adjusting means on the basis of the light emitted from said observation light source and a signal output from said image-capturing means.

2. An ophthalmological image-taking apparatus according to claim 1, further comprising gain control means for controlling the gain of an amplifier to obtain an amplified signal output from said image capturing means,
    wherein said emission control means controls said second adjusting means in accordance with the gain of the amplifier.

3. An ophthalmological image-taking apparatus according to claim 2, wherein said image-capturing means is used for taking an image of the eye fundus illuminated by said flash source.

4. A method for changing a gain of an amplifier for obtaining an amplified signal output from image-capturing means in an ophthalmological image-taking apparatus comprising an observation light source configured and positioned to illuminate an eye fundus during observation, a flash source configured and positioned to illuminate the eye fundus when taking a still image, and the image-capturing means for capturing a moving image illuminated by the observation light source during observation or the still image illuminated by the flash source when taking the still image, the method for changing the gain comprising the steps of:
    storing the gain of the amplifier;
    controlling the gain of the amplifier to obtain the amplified signal output from the image-capturing means in accordance with the gain stored in said gain storing step;
    determining the level of the amplified signal output from the image-capturing means when taking the image; and
    changing the gain stored in the gain storing step in accordance with a result determined in said determining step.

5. An ophthalmological image-taking apparatus comprising:
    an observation light source configured and positioned to illuminate an eye fundus during observation;
    an image-capturing element configured and positioned to capture an image of the eye fundus illuminated by said observation light source;
    a control circuit, connected to said observation light source and configured to adjust the amount of light emitted from said observation light source;
    a flash source configured and positioned to illuminate the eye fundus when taking a still image;

a source of electric power connected to said flash source and configured to adjust the amount of light emitted from said flash source; and a flash source emission control circuit connected to said source of electric power and configured to control said source of electric power on the basis of the light emitted from said observation light source and a signal output from said image-capturing element.

6. An ophthalmological image-taking apparatus according to claim 5, wherein said source of electric power is a capacitor.

7. An ophthalmological image-taking apparatus according to claim 5, further comprising:

an amplifier connected to said image-capturing element and configured to amplify the signal output from said image-capturing element; and a gain setting circuit, connected to said amplifier and configured to control the gain of said amplifier, wherein said flash source emission control circuit is configured to control said source of electric power in accordance with the gain.

8. An ophthalmological image-taking apparatus according to claim 7, wherein said image-capturing element is used for taking an image of the eye fundus illuminated by said flash source.

9. A device for changing a gain of an amplifier for obtaining a signal output from an image-capturing means in an ophthalmological image-taking apparatus comprising an observation light source configured and positioned to illuminate an eye fundus during observation, a flash source configured and positioned to illuminate the eye fundus when taking a still image, and the image-capturing means for capturing a moving image illuminated by the observation light source during observation or still image illuminated by the flash source when taking the still image, the device for changing the gain comprising:

means for storing the gain of the amplifier;

means for controlling the gain of the amplifier to obtain an amplified signal output from the image-capturing means in accordance with the gain stored in said gain storing means;

means for determining the level of the amplified signal output from the image-capturing means when taking the image; and means for changing the gain stored in the gain storing means in accordance with a result determined by said determined means.

10. A device for changing a gain of an amplifier for amplifying a signal output from an image-capturing element in an ophthalmological image-taking apparatus which includes an observation light source configured and positioned to illuminate an eye fundus during observation, a flash source configured and positioned to illuminate the eye fundus when taking a still image, and the image-capturing element configured and positioned to capture a moving image illuminated by the observation light source during observation or the still image illuminated by the flash source when taking the still image, comprising:

a circuit element, configured to store the gain for amplifying the signal output from the image-capturing element;

a gain setting circuit, connected to said circuit element and configured to control the gain of the amplifier in accordance with the gain stored in said circuit element; and a signal determination circuit, connected to the amplifier and configured to determine the level of an amplified signal output from the amplifier when taking the image, wherein the amplfier changes the gain stored in said circuit element in accordance with a result determined by said signal determination circuit.

11. An ophthalmological image-taking apparatus comprising:

an observation light source configured and positioned to illuminate an eye fundus during observation;

image-capturing means, including an image-capturing element and amplifying means for amplifying a signal from said image-capturing element, for capturing an image of the eye fundus;

adjusting means for adjusting the amount of light emitted from said observation light source; and gain control means for controlling a gain of said amplifying means on the basis of the light emitted from said observation light source and a signal output from said image-capturing means.

12. An ophthalmologic image-taking apparatus according to claim 11, further comprising a flash source configured and positioned to illuminate the eye fundus when taking a still image; and second adjusting means for adjusting the amount of light emitted from said flash source, wherein said gain control means controls the gain of said amplifying means on the basis of the amount of the light to be emitted from said flash source.

* * * * *

UNITED STATES PATENT AND TRADEMARK OFFICE
CERTIFICATE OF CORRECTION

PATENT NO.       : 6,832,835 B2                                        Page 1 of 1
APPLICATION NO.  : 10/263956
DATED            : December 21, 2004
INVENTOR(S)      : Kazuhiro Matsumoto It is certified that error appears in the above-identified patent and that said Letters Patent is hereby corrected as shown below:

COLUMN 2
Line 32, "an" should read --and an--.
Line 33, "light are" should read --light, which are--.

COLUMN 11
Line 48, "determined" should read --determining--.

COLUMN 12
Line 40, "ophthalmologic" should read --ophthalmological--.

Signed and Sealed this

Fifth Day of June, 2007

JON W. DUDAS
*Director of the United States Patent and Trademark Office*